(12) United States Patent
Manku et al.

(10) Patent No.: US 8,673,325 B1
(45) Date of Patent: *Mar. 18, 2014

(54) COSMETIC COMPOSITIONS COMPRISING EPA AND SALICYLIC ACID AND METHODS OF MAKING AND USING SAME

(71) Applicant: Dignity Sciences Limited, Leopardstown (IE)

(72) Inventors: Mehar Manku, Birmingham (GB); John Climax, Leopardstown (IE); David Coughlan, Leopardstown (IE)

(73) Assignee: Dignity Sciences Limited (IE)

( * ) Notice: Subject to any disclaimer, the term of this patent is extended or adjusted under 35 U.S.C. 154(b) by 0 days.

This patent is subject to a terminal disclaimer.

(21) Appl. No.: 13/906,673

(22) Filed: May 31, 2013

Related U.S. Application Data

(60) Provisional application No. 61/697,631, filed on Sep. 6, 2012.

(51) Int. Cl.
*A61K 9/00* (2006.01)

(52) U.S. Cl.
USPC .......................................................... 424/400

(58) Field of Classification Search
None
See application file for complete search history.

(56) References Cited

U.S. PATENT DOCUMENTS

| | | |
|---|---|---|
| 5,312,834 A | 5/1994 | Yeo |
| 5,409,955 A | 4/1995 | Bockow et al. |
| 5,709,855 A * | 1/1998 | Bockow ........................ 424/93.7 |

OTHER PUBLICATIONS

Chen, Yung-Chih et al.; "Therapeutic Effect of Topical Gamma-Linolenic Acid on Refractory Uremic Pruritus", American Journal of Kidney Diseases, vol. 48, No. 1, Jul. 2006, pp. 69-76.

Desbois, A. P. et al.; "Antibacterial free fatty acids: activities, mechanisms of action and biotechnological potential" Appl Microbiol Biotechnol , (2010) vol. 85 pp. 1629-1642.

Dewsbury, C. E. et al.; "Topical eicosapentaenoic acid (EPA) in the treatment of psoriasis" British Journal of Dermatology (1989) 120, p. 581.

Horrobin, D. F.; "Nutritional and Medical Importance of Gamma-Linolenic Acid"; Prog. lipid Res. vol. 31, No. 2. pp. 163-194, 1992.

Kanehara, S. et al.; "Undershirts coated with borage oil alleviate the symptoms of atopic dermatitis in children" ; EJD, vol. 17, No. 5, Sep.-Oct. 2007, pp. 448-449.

Kawamura, A. et al.; "Dietary Supplemental of Gamma-Linolenic Acid Improves Skin Parameters in Subjects with Dry Skin and Atopic Dermatitis"; Journal of Oleo Science; vol. 60, No. 12, pp. 597-607, 2011.

Miller, C. C. et al.; Induction of Epidermal Hyperproliferation by Topical n-3 Polyunsaturated Fatty Acids on Guinea Pig Skin Linked to Decreased Levels of 13-Hydroxyoctadecadienoic Acid (13-Hode); The Journal of Investigative Dermatology, vol. 94, No. 3, Mar. 1990, pp. 353-358.

Stillman, M. A. et al.; "Relative irritancy of free fatty acids of different chain length"; Contact Dermatitis, 1975, 1, pp. 65-69.

Thiboutot, D. et al.; New insights into the management of acne: An update from Global Alliance to Improve Outcomes in Acne Group; J Am Acad Dermatol, May 2009, vol. 60, No. 5, pp. S1-S50.

Uchida, A. et al.; "Antibacterial and Antialgal Substances Produced by the Dinoflagellate Peridinium bipes"; Nippon Sisan Gakkaishi (Formerly Bull. Japan. Soc. Sci. Fish.), vol. 54, No. 11, (1998), pp. 1941-1945.

Watanabe, T. et al.; "The effect of a newly developed ointment containing eicosapentaenoic acid and docosahexaenoic acid in the treatment of atopic dermatitis" ; The Journal of Medicine Investigation; vol. 46, 1999, 173-177.

Zulfakar, M. H. et al.; "Is there a role for topically delivered eicosapentaenoic acid in the treatment of psoriasis"; Eur J Dermatol, 2007, vol. 17, No. 4, pp. 284-291.

\* cited by examiner

*Primary Examiner* — Robert T Crow
*Assistant Examiner* — Doan Phan
(74) *Attorney, Agent, or Firm* — Cantor Colburn LLP

(57) ABSTRACT

The present disclosure is directed generally to cosmetic compositions comprising EPA free acid and salicylic acid. In some embodiments, the cosmetic compositions have a cosmetically acceptable odor.

20 Claims, 1 Drawing Sheet

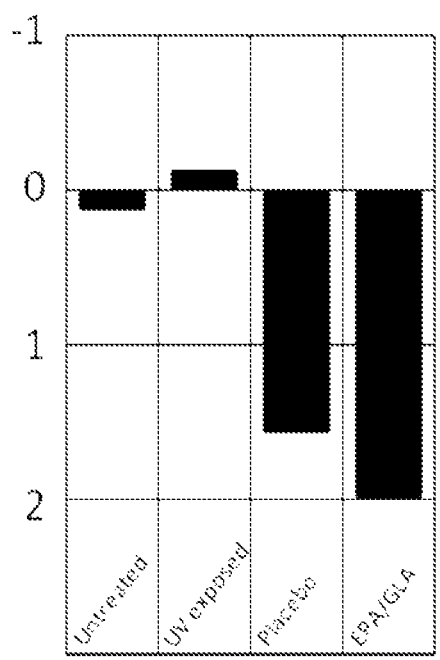

COSMETIC COMPOSITIONS COMPRISING EPA AND SALICYLIC ACID AND METHODS OF MAKING AND USING SAME

CROSS REFERENCE TO RELATED APPLICATIONS

This application claims the benefit of U.S. Provisional Application Ser. No. 61/697,631, filed Sep. 6, 2012, which is hereby incorporated by reference in its entirety.

FIELD

The disclosure generally relates to cosmetic compositions comprising eicosapentaenoic free acid and salicylic acid, and methods of manufacture and use thereof.

BACKGROUND

Compositions which include long chain free fatty acid components—including those for topical and/or cosmetic use—are well-known to develop unpleasant odors. It is believed that decomposition (e.g., oxidation) of the free fatty acid component(s) is the source of the odor. One strategy to avoid odor formation has been to use derivatives of the fatty acids, for example esters, triglycerides, etc. However, preparing derivatives of free fatty acids from source materials is time-consuming, costly, and in some cases attenuates the desired activity of the compounds. On the other hand, offensive odors in personal care products contribute to non-compliance with a recommended treatment schedule. In addition, derivatives of free fatty acids such as alkyl esters are generally much less soluble in aqueous compositions. Especially for cosmetic compositions, then, the decreased hydrophilicity of fatty acid derivatives is undesirable as organic co-solvents tend to be harsher on the skin than water-based compositions. Accordingly, there exists a need for compositions comprising free fatty acids without an associated unpleasant odor.

SUMMARY

The present disclosure provides compositions comprising free fatty acid agents including, for example, eicosapentaenoic free acid and gamma-linolenic free acid. In some embodiments, the eicosapentaenoic free acid and the gamma-linolenic free acid are present in a weight ratio of about 2:1 to about 8:1, for example about 4:1. In some embodiments, the eicosapentaenoic free acid is present in an amount of about 0.5 wt. % to about 8 wt. %, about 0.8 wt. % to about 4 wt. %, about 0.815 wt. %, about 1.631 wt. %, or about 4.080 wt. %. In some embodiments, the gamma-linolenic free acid is present in an amount of about 0.1 wt. % to about 3 wt. %, about 0.2 wt. % to about 1.5 wt. %, about 0.285 wt. %, about 0.570 wt. %, or about 1.425 wt. %. In some embodiments, the compositions further comprise one or more excipients. Such compositions are free of unpleasant odors typically associated with compositions comprising free fatty acids and thus are useful as topical, cosmetic and/or personal care products.

In some embodiments, the composition further comprises one or more excipients selected from the group consisting of: solvents, sequestrants, humectants, thickening agents, emulsifiers, emollients, adsorbing agents, preservatives, fragrances, antioxidants, pH modifiers, texturizing agents, and combinations thereof. In some embodiments, the excipients comprise: water, Glycerine Veg. PH EUR 99.5% (Glycerin), Trilon B (Disodium EDTA), Cosmedia SP (sodium polyacrylate), Lincol BAS (C12-15 alkyl benzoate), Lincol SN (cetearyl isononanoate), Burro Di KARITE (butyrospermum parkii butter), Euxyl PE 9010 (phenoxyethanol & ethylhexylglycerin), Profumo Fiori D'acqua 85328, Lipochroman (dimethylmethoxy chromanol), Ascorbyl palmitate, Imwitor 372P (glyceryl stearate citrate), Cutina GMS/Bergabest GS40/Lincol GMS (glyceryl stearate), Lanette 22/Vegarol 22/Akest AB/Nafol 1822C (behenyl alcohol), Sodium hydroxide and Dry-Flo PC (aluminum starch octenylsuccinate). In some embodiments, the excipients comprise: water, Trilon B (Disodium EDTA), Glycerine Veg. PH EUR 99.5% (Glycerin), Silwax WS (PEG-8-dimethicone), Gransil EPS (polysilicone-11 & laureth 12), Velvesil DM (dimethicone & detearyl dimethicone crosspolymer), Cosmedia Silc (silica), Granpowder USQ (polyurethane and polymethylsilsesquioxane), Cosmedia SP (sodium polyacrylate), Cetiol Sensoft (propylheptyl caprylate), Euxyl PE 9010 (phenoxyethanol & ethylhexylglycerin), Profumo Fiori D'acqua 85328 and Lipochroman (dimethylmethoxy chromanol). In some embodiments, the excipients comprise: water, Trilon B (Disodium EDTA), Glycerine Veg. PH EUR 99.5% (Glycerin), Silwax WS (PEG-8-dimethicone), Gransil EPS (polysilicone-11 & laureth 12), Velvesil DM (dimethicone & detearyl dimethicone crosspolymer), Cosmedia Silc (silica), Aristoflex AVC (polymeric sulphonic acid), Cetiol Sensoft (propylheptyl caprylate), Euxyl PE 9010 (phenoxyethanol & ethylhexylglycerin), Profumo Fiori D'acqua 85328 and Aperoxide TLA (tocopherol, lecithin, ascorbyl palmitate and citric acid).

The present disclosure also provides methods for treating and/or preventing a condition (e.g., a skin condition such as dryness, roughness, wrinkles, sunburn, seborrheic dermatitis, acne etc.) in a subject in need thereof comprising administering to a subject a composition comprising a therapeutically effective amount of eicosapentaenoic free acid and gamma-linolenic free acid.

In some embodiments, the compositions are formulated for topical administration, such as a cream, an ointment, an oil, a liniment, a powder, an aerosol, a shampoo, or any other form reasonably adapted for topical administration.

These and other embodiments of the invention are described in further detail below.

BRIEF DESCRIPTION OF THE FIGURES

FIG. 1 shows skin hydration changes from Day 1 to Day 15 for skin treated with a composition consistent with the present disclosure compared to skin treated with placebo, untreated irradiated skin, and untreated non-irradiated skin.

DETAILED DESCRIPTION

The present disclosure provides compositions (e.g., cosmetic compositions) and formulations that comprise fatty acid agents including, for example, eicosapentaenoic free acid and gamma-linolenic free acid, said compositions free of unpleasant odors commonly associated with free fatty acid compounds. Such agents have been found to positively affect (e.g., treat and/or prevent) skin conditions such as dryness, roughness, wrinkles, sunburn, seborrheic dermatitis, acne etc. Given this capacity, the compositions and formulations disclosed herein may be used in the treatment and/or prevention of skin conditions.

While the present disclosure is capable of being embodied in various forms, the description below of several embodiments is made with the understanding that the present disclosure is to be considered as an exemplification of the disclosure, and is not intended to limit the disclosure to the specific embodiments illustrated. Headings are provided for convenience only and are not to be construed to limit the disclosure in any manner. Embodiments illustrated under any heading may be combined with embodiments illustrated under any other heading.

The use of numerical values in the various quantitative values specified in this application, unless expressly indicated otherwise, are stated as approximations as though the minimum and maximum values within the stated ranges were both preceded by the word "about." Also, the disclosure of ranges is intended as a continuous range including every value between the minimum and maximum values recited as well as any ranges that can be formed by such values. Also disclosed herein are any and all ratios (and ranges of any such ratios) that can be formed by dividing a disclosed numeric value into any other disclosed numeric value. Accordingly, the skilled person will appreciate that many such ratios, ranges, and ranges of ratios can be unambiguously derived from the numerical values presented herein and in all instances such ratios, ranges, and ranges of ratios represent various embodiments of the present disclosure.

Eicosapentaenoic acid, an omega-3 fatty acid also known as all-cis-5,8,11,14,17-eicosapentaenoic acid or (5Z,8Z,11Z,14Z,17Z)-5,8,11,14,17-icosapentaenoic acid, is typically derived from fish oil and/or algae. As used herein, the term "EPA" refers to eicosapentaenoic acid in its free acid form unless otherwise expressly stated. In some embodiments of the present disclosure, EPA is provided in a composition comprising at least about 95% by weight EPA, for example at least about 95% by weight EPA, at least about 96% by weight EPA, at least about 97% by weight EPA, at least about 98% by weight EPA, at least about 98.1% by weight EPA, or at least about 99% by weight EPA.

Gamma-linolenic acid, an omega-6 fatty acid also known as γ-linolenic acid, gamolenic acid, all-cis-6,9,12-octadecatrienoic acid, is generally derived from vegetable oils and seed oils. As used herein, the term "GLA" refers to gamma-linolenic acid in its free acid form unless otherwise expressly stated. In some embodiments of the present disclosure, GLA is provided in a composition comprising at least about 70% by weight GLA, for example at least about 70% by weight GLA, at least about 70.2% by weight GLA, at least about 71% by weight GLA, at least about 72% by weight GLA, at least about 73% by weight GLA, at least about 74% by weight GLA, at least about 75% by weight GLA, at least about 76% by weight GLA, at least about 77% by weight GLA, at least about 78% by weight GLA, at least about 79% by weight GLA, at least about 80% by weight GLA, at least about 81% by weight GLA, at least about 82% by weight GLA, at least about 83% by weight GLA, at least about 84% by weight GLA, at least about 85% by weight GLA, at least about 86% by weight GLA, at least about 87% by weight GLA, at least about 88% by weight GLA, or at least about 89% by weight GLA. In some embodiments, the GLA is provided as an oil comprising: about 70% GLA, about 5.5% Palmitic acid (16:0), about 3.6% Stearic acid, about 3.4% Oleic acid, about 13.1% Linoleic acid, about 1.6% Icosenoic acid, and about 1.8% Docosenoic acid.

As used herein, the term "animal" means any animal that has a need for preventing or treating a skin condition.

As used herein, the term "therapeutically effective amount" means an amount of a compound of the invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

As used herein, the terms "treating", "treat", and "treatment" embrace both preventative, i.e., prophylactic, and palliative treatment.

As used herein, the term "cosmetic composition" means a composition that is formulated for use as a cosmetic, or a formulation that is not specifically formulated for use as a cosmetic but could reasonably be used as a cosmetic without further modification.

As used herein, the terms "free of unpleasant odor" and "cosmetically acceptable odor" are used interchangeably and mean generally that a majority or large majority of subjects rate or would rate the composition as having no fish odor or low fish odor.

As used herein the term "acne" herein refers to any disease or disorder of the skin that presents with one or more acneiform eruptions such as papules, pustules, cysts, and the like. Non-limiting examples of acne include acne vulgaris, acne necrotica, halogen acne, chloracne, occupational acne, oil acne, tar acne, acne aestivalis, tropical acne, acne cosmetica, pomade acne, acne keloidalis nuchae, acne mechanica, excoriated acne, acne medicamentosa, infantile acne, neonatal acne, acne conglobata, acne fulminans, acne miliaris necrotica, miliaris disseminatus faciei, and other skin disorders associated with acneiform eruptions.

As used herein, "wrinkles" includes small ridges or furrows in skin, commonly due to age, fatigue, sun exposure, exposure to environmental conditions such as heat, wind and/or dust, and/or behavioral conditions such as smoking.

In some embodiments, the EPA is present in an amount of about 0.4 wt. % to about 8 wt. %, for example about 0.4 wt. %, about 0.5 wt. %, about 0.815 wt. %, about 1 wt. %, about 1.5 wt. %, about 1.631 wt. %, about 2 wt. %, about 2.5 wt. %, about 3 wt. %, about 3.5 wt. %, about 4 wt. %, about 4.5 wt. %, about 5 wt. %, about 5.5 wt. %, about 6 wt. %, about 6.5 wt. %, about 7 wt. %, about 7.5 wt. %, or about 8 wt. %. The term "the EPA is present in an amount" refers herein to the amount of EPA free acid in the composition. For example, in embodiments wherein the EPA is provided as an EPA composition comprising 98.1 wt. % EPA, the EPA composition is added to the cosmetic composition in an amount sufficient to provide EPA in an amount of about 0.5 wt. % to about 8 wt. %, taking into account the actual amount of EPA in the EPA composition. In some embodiments, the EPA is present in an amount of about 0.8 wt. % to about 4 wt. %, for example about 0.8 wt. %, about 0.815 wt. %, about 1 wt. %, about 1.25 wt. %, about 1.5 wt. %, about 1.631 wt. %, about 1.75 wt. %, about 2 wt. %, about 2.25 wt. %, about 2.5 wt. %, about 2.75 wt. %, about 3 wt. %, about 3.25 wt. %, about 3.5 wt. %, about 3.75 wt. %, or about 4 wt. %. In some embodiments, the EPA is present in an amount of about 0.815 wt. %. In some embodiments, the EPA is present in an amount of about 1.631 wt. %. In some embodiments, the EPA is present in an amount of about 4.080 wt. %.

In some embodiments, the GLA is present in an amount of about 0.1 wt. % to about 3 wt. %, for example about 0.1 wt. %, about 0.25 wt. %, about 0.285 wt. %, about 0.5 wt. %, about 0.570 wt. %, about 0.75 wt. %, about 1 wt. %, about 1.25 wt. %, about 1.425 wt. %, about 1.5 wt. %, about 1.75 wt. %, about 2 wt. %, about 2.25 wt. %, about 2.5 wt. %, about 2.75 wt. %, about 3 wt. %. The term "the GLA is present in an amount" refers herein to the amount of GLA free acid in the composition. For example, in embodiments wherein the GLA is provided as a GLA composition comprising 70.2 wt. % GLA, the GLA composition is added to the cosmetic composition in an amount sufficient to provide GLA in an amount of about 0.1 wt. % to about 3 wt. %, taking into account the actual amount of GLA in the GLA composition. In some embodiments, the GLA is present in an amount of about 0.2 wt. % to about 1.5 wt. %, for example about 0.2 wt. %, about 0.25 wt. %, about 0.285 wt. %, about 0.3 wt. %, about 0.35 wt. %, about 0.4 wt. %, about 0.45 wt. %, about 0.5 wt. %, about 0.55 wt. %, about 0.6 wt. %, about 0.65 wt. %, about 0.7 wt. %, about 0.75 wt. %, about 0.8 wt. %, about 0.85 wt. %, about 0.9 wt. %, about 1 wt. %, about 1.05 wt. %, about 1.1 wt. %, about 1.15 wt. %, about 1.2 wt. %, about 1.25 wt. %, about 1.3 wt. %, about 1.35 wt. %, about 1.4 wt. %, about 1.45 wt. %, or about 1.5 wt. %. In some embodiments, the GLA is present in an amount of about 0.285 wt. %. In some embodiments, the GLA is present in an amount of about 0.570 wt. %. In some embodiments, the GLA is present in an amount of about 1.425 wt. %.

In some embodiments the GLA is provided as a GLA oil comprising about 70% GLA, by weight, and one or more of Palmitic acid, Stearic acid, Oleic acid, Linoleic acid, Icosenoic acid, and Docosenoic acid, wherein the GLA oil is added to the cosmetic composition in an amount sufficient to provide GLA in an amount of about 0.1 wt. % to about 3 wt. %, taking into account the actual amount of GLA in the GLA composition. In some embodiments, the GLA is present in an amount of about 0.2 wt. % to about 1.5 wt. %, for example about 0.2 wt. %, about 0.25 wt. %, about 0.285 wt. %, about 0.3 wt. %, about 0.35 wt. %, about 0.4 wt. %, about 0.45 wt. %, about 0.5 wt. %, about 0.55 wt. %, about 0.6 wt. %, about 0.65 wt. %, about 0.7 wt. %, about 0.75 wt. %, about 0.8 wt. %, about 0.85 wt. %, about 0.9 wt. %, about 1 wt. %, about 1.05 wt. %, about 1.1 wt. %, about 1.15 wt. %, about 1.2 wt. %, about 1.25 wt. %, about 1.3 wt. %, about 1.35 wt. %, about 1.4 wt. %, about 1.45 wt. %, or about 1.5 wt. %. In some embodiments, the GLA is present in an amount of about 0.285 wt. %. In some embodiments, the GLA is present in an amount of about 0.570 wt. %. In some embodiments, the GLA is present in an amount of about 1.425 wt. %.

In some embodiments the GLA is provided as a GLA oil comprising about 70 wt. % GLA, about 5.5 wt. % Palmitic acid, about 3.6 wt. % Stearic acid, about 3.4 wt. % Oleic acid, about 13.1 wt. % Linoleic acid, about 1.6 wt. % Icosenoic acid, and about 1.8 wt. % Docosenoic acid, wherein the GLA oil is added to the cosmetic composition in an amount sufficient to provide GLA in an amount of about 0.1 wt. % to about 3 wt. %, taking into account the actual amount of GLA in the GLA composition. In some embodiments, the GLA is present in an amount of about 0.2 wt. % to about 1.5 wt. %, for example about 0.2 wt. %, about 0.25 wt. %, about 0.285 wt. %, about 0.3 wt. %, about 0.35 wt. %, about 0.4 wt. %, about 0.45 wt. %, about 0.5 wt. %, about 0.55 wt. %, about 0.6 wt. %, about 0.65 wt. %, about 0.7 wt. %, about 0.75 wt. %, about 0.8 wt. %, about 0.85 wt. %, about 0.9 wt. %, about 1 wt. %, about 1.05 wt. %, about 1.1 wt. %, about 1.15 wt. %, about 1.2 wt. %, about 1.25 wt. %, about 1.3 wt. %, about 1.35 wt. %, about 1.4 wt. %, about 1.45 wt. %, or about 1.5 wt. %. In some embodiments, the GLA is present in an amount of about 0.285 wt. %. In some embodiments, the GLA is present in an amount of about 0.570 wt. %. In some embodiments, the GLA is present in an amount of about 1.425 wt. %.

In one embodiment, a cosmetic composition according to the present disclosure comprises EPA, GLA and one or more excipients. In some embodiments, the EPA and GLA are present in amounts such that the weight ratio of EPA to GLA is about 2:1 to about 8:1, for example about 2:1, about 3:1, about 4:1, about 5:1, about 6:1, about 7:1, or about 8:1.

In some embodiments, the EPA and GLA are present in a weight ratio of about 4:1. Thus, in such embodiments, EPA is present in an amount of about 0.5 wt. % to about 8 wt. %, and GLA is present in an amount of about 0.125 wt. % to about 2 wt. %. Alternatively, GLA is present in such embodiments in an amount of about 0.1 wt. % to about 2 wt. %, and EPA is present in an amount of about 0.4 wt. % to about 8 wt. %.

In some embodiments, a cosmetic composition of the present disclosure comprises about 0.815 wt. % to 4.08 wt. % EPA, about 0.285 wt. % to about 1.425 wt. % GLA, and one or more cosmetically acceptable excipients. In some embodiments, the EPA and GLA are present in a weight ratio of about 4:1. In some embodiments, the excipients are selected from the group consisting of: solvents, sequestrants, humectants, thickening agents, emulsifiers, emollients, adsorbing agents, preservatives, fragrances, antioxidants, pH modifiers, texturizing agents, and combinations thereof.

In some embodiments, a composition of the present disclosure additionally comprises an antimicrobial agent. In some embodiments, the antimicrobial agent is selected from the group consisting of salicylic acid, azelaic acid, furosemide, benzoyl peroxide and neomycin. In some embodiments, the antimicrobial agent is present in an amount less than an amount generally considered to be effective (e.g., a sub-therapeutic concentration). In some embodiments, the antimicrobial agent is present in an amount about the same as, or the same as, a generally recognized therapeutic dose.

Cosmetic compositions of the present disclosure further comprise a solvent. In some embodiments, the solvent comprises water. In some embodiments, the solvent comprises water. In embodiments of the present disclosure, the solvent is present in an amount of about 50 wt. % to about 85 wt. %, for example about 50 wt. %, about 51 wt. %, about 52 wt. %, about 53 wt. %, about 54 wt. %, about 55 wt. %, about 56 wt. %, about 57 wt. %, about 58 wt. %, about 59 wt. %, about 60 wt. %, about 61 wt. %, about 62 wt. %, about 63 wt. %, about 64 wt. %, about 65 wt. %, about 66 wt. %, about 67 wt. %, about 68 wt. %, about 69 wt. %, about 70 wt. %, about 71 wt. %, about 72 wt. %, about 73 wt. %, about 74 wt. %, about 75 wt. %, about 76 wt. %, about 77 wt. %, about 78 wt. %, about 79 wt. %, about 80 wt. %, about 81 wt. %, about 82 wt. %, about 83 wt. %, about 84 wt. %, or about 85 wt. %. In some embodiments, the solvent is present in an amount of about 76.685 wt. %. In some embodiments, the solvent is present in an amount of about 80.289 wt. %. In some embodiments, the solvent is present in an amount of about 81.59 wt. %. In some embodiments, the solvent is present in an amount of about 77.645 wt. %. In some embodiments, the solvent is present in an amount of about 81.249 wt. %. In some embodiments, the solvent is present in an amount of about 82.55 wt. %. In some embodiments, the solvent is present in an amount of about 72.875 wt. %. In some embodiments, the solvent is present in an amount of about 76.179 wt. %. In some embodiments, the solvent is present in an amount of about 77.28 wt. %.

In some embodiments, a cosmetic composition of the present disclosure further comprises a sequestrant. Any sequestrant suitable for use in a cosmetic composition is contemplated. In some embodiments, the sequestrant is one or more of tetrasodium EDTA (TRILON B), disodium EDTA (TRILON B), calcium disodium EDTA, glucono delta-lactone, sodium gluconate, potassium gluconate, sodium tripolyphosphate, sodium hexametaphosphate, and combinations thereof. In some embodiments, the sequestrant is tetrasodium EDTA. In some embodiments, the sequestrant is disodium EDTA. In some embodiments, the sequestrant is present in an amount of about 0.01 wt. % to about 0.5 wt. %, for example about 0.01 wt. %, about 0.02 wt. %, about 0.03 wt. %, about 0.04 wt. %, about 0.05 wt. %, about 0.06 wt. %, about 0.07 wt. %, about 0.08 wt. %, about 0.09 wt. %, about 0.1 wt. %, about 0.11 wt. %, about 0.12 wt. %, about 0.13 wt. %, about 0.14 wt. %, about 0.15 wt. %, about 0.16 wt. %, about 0.17 wt. %, about 0.18 wt. %, about 0.19 wt. %, about 0.20 wt. %, about 0.21 wt. %, about 0.22 wt. %, about 0.23 wt. %, about 0.24 wt. %, about 0.25 wt. %, about 0.26 wt. %, about 0.27 wt. %, about 0.28 wt. %, about 0.29 wt. %, about 0.30 wt. %, about 0.31 wt. %, about 0.32 wt. %, about 0.33 wt. %, about 0.34 wt. %, about 0.35 wt. %, about 0.36 wt. %, about 0.37 wt. %, about 0.38 wt. %, about 0.39 wt. %, about 0.40 wt. %, about 0.41 wt. %, about 0.42 wt. %, about 0.43 wt. %, about 0.44 wt. %, about 0.45 wt. %, about 0.46 wt. %, about 0.47 wt. %, about 0.48 wt. %, about 0.49 wt. %, or about 0.5 wt. %. In some embodiments, the sequestrant is present in an amount of about 0.10 wt. %.

In some embodiments, a cosmetic composition of the present disclosure further comprises a humectant. Any humectant suitable for use in a cosmetic composition is contemplated. In some embodiments, the humectant is one or more of propylene glycol, glyceryl triacetate, vinyl alcohol, neoagarobiose, a sugar polyol, a polymeric polyol, quillaia, lactic acid, urea, glycerine, aloe vera gel, MP Diol, an alpha-hydroxy acid, honey, and combinations thereof. In some embodiments, the humectant is a glycerine, such as Glycerine Veg. PH EUR. In some embodiments, the humectant is present in an amount of about 0.5 wt. % to about 5 wt. %, for example about 0.5 wt. %, about 0.6 wt. %, about 0.7 wt. %, about 0.8 wt. %, about 0.9 wt. %, about 1 wt. %, about 1.1 wt. %, about 1.2 wt. %, about 1.3 wt. %, about 1.4 wt. %, about 1.5 wt. %, about 1.6 wt. %, about 1.7 wt. %, about 1.8 wt. %, about 1.9 wt. %, about 2 wt. %, about 2.1 wt. %, about 2.2 wt. %, about 2.3 wt. %, about 2.4 wt. %, about 2.5 wt. %, about 2.6 wt. %, about 2.7 wt. %, about 2.8 wt. %, about 2.9 wt. %, about 3 wt. %, about 3.1 wt. %, about 3.2 wt. %, about 3.3 wt. %, about 3.4 wt. %, about 3.5 wt. %, about 3.6 wt. %, about 3.7 wt. %, about 3.8 wt. %, about 3.9 wt. %, about 4 wt. %, about 4.1 wt. %, about 4.2 wt. %, about 4.3 wt. %, about 4.4 wt. %, about 4.5 wt. %, about 4.6 wt. %, about 4.7 wt. %, about 4.8 wt. %, about 4.9 wt. %, or about 5 wt. %. In some embodiments, the humectant is present in an amount of about 3 wt. %.

In some embodiments, a cosmetic composition of the present disclosure further comprises a texturizing agent. Any texturizing agent suitable for use in a cosmetic composition is contemplated. In some embodiments, the texturizing agent is one or more of PEG-8-dimethicone (SILWAX WS), polysilicone-11, laureth-12, a crosspolymer of dimethicone and detearyl dimethicone (VELVESIL DM), silica (COSMEDIA SILC), polyurethane, polymethylsilsesquioxane, a mixture of polysilicone-11 and laureth-12 (GRANSIL EPS), a mixture of polyurethane and polymethylsilsesquioxane (GRANPOWDER USQ), and combinations thereof. In some embodiments, the texturizing agent is a combination of SILWAX WS, GRANSIL EPS, VELVESIL DM, COSMEDIA SILC, and GRANPOWDER USQ. In some embodiments, the cosmetic composition does not include a texturizing agent. In some embodiments, the texturizing agent is present in an amount of about 0.5 wt. % to about 15 wt. %, for example about 0.5 wt. %, about 0.75 wt. %, about 1 wt. %, about 1.25 wt. %, about 1.5 wt. %, about 1.75 wt. %, about 2 wt. %, about 2.25 wt. %, about 2.5 wt. %, about 2.75 wt. %, about 3 wt. %, about 3.25 wt. %, about 3.5 wt. %, about 3.75 wt. %, about 4 wt. %, about 4.25 wt. %, about 4.5 wt. %, about 4.75 wt. %, about 5 wt. %, about 5.25 wt. %, about 5.5 wt. %, about 5.75 wt. %, about 6 wt. %, about 6.25 wt. %, about 6.5 wt. %, about 6.75 wt. %, about 7 wt. %, about 7.25 wt. %, about 7.5 wt. %, about 7.75 wt. %, about 8 wt. %, about 8.25 wt. %, about 8.5 wt. %, about 8.75 wt. %, about 9 wt. %, about 9.25 wt. %, about 9.5 wt. %, about 9.75 wt. %, about 10 wt. %, about 10.25 wt. %, about 10.5 wt. %, about 10.75 wt. %, about 11 wt. %, about 11.25 wt. %, about 11.5 wt. %, about 11.75 wt. %, about 12 wt. %, about 12.25 wt. %, about 12.5 wt. %, about 12.75 wt. %, about 13 wt. %, about 13.25 wt. %, about 13.5 wt. %, about 13.75 wt. %, about 14 wt. %, about 14.25 wt. %, about 14.5 wt. %, about 14.75 wt. %, or about 15 wt. %. In some embodiments, the texturizing agent is present in an amount of about 8 wt. %. In some embodiments, the texturizing agent is present in an amount of about 9 wt. %.

In some embodiments, a cosmetic composition of the present disclosure further comprises a thickening agent. Any thickening agent suitable for use in a cosmetic composition is contemplated. In some embodiments, the thickening agent is one or more of sodium polyacrylate (COSMEDIA SP), polymeric sulphonic acid (ARISTOFLEX AVC), or combinations thereof. In some embodiments, the thickening agent is sodium polyacrylate (COSMEDIA SP). In some embodiments, the thickening agent is polymeric sulphonic acid (ARISTOFLEX AVC). In some embodiments, the thickening agent is present in an amount of about 0.1 wt. % to about 5 wt. %, for example about 0.1 wt. %, about 0.2 wt. %, about 0.3 wt. %, about 0.4 wt. %, about 0.5 wt. %, about 0.6 wt. %, about 0.7 wt. %, about 0.8 wt. %, about 0.9 wt. %, about 1 wt. %, about 1.1 wt. %, about 1.2 wt. %, about 1.3 wt. %, about 1.4 wt. %, about 1.5 wt. %, about 1.6 wt. %, about 1.7 wt. %, about 1.8 wt. %, about 1.9 wt. %, about 2 wt. %, about 2.1 wt. %, about 2.2 wt. %, about 2.3 wt. %, about 2.4 wt. %, about 2.5 wt. %, about 2.6 wt. %, about 2.7 wt. %, about 2.8 wt. %, about 2.9 wt. %, about 3 wt. %, about 3.1 wt. %, about 3.2 wt. %, about 3.3 wt. %, about 3.4 wt. %, about 3.5 wt. %, about 3.6 wt. %, about 3.7 wt. %, about 3.8 wt. %, about 3.9 wt. %, about 4 wt. %, about 4.1 wt. %, about 4.2 wt. %, about 4.3 wt. %, about 4.4 wt. %, about 4.5 wt. %, about 4.6 wt. %, about 4.7 wt. %, about 4.8 wt. %, about 4.9 wt. %, or about 5 wt. %. In some embodiments, the thickening agent is present in an amount of about 0.5 wt. %. In some embodiments, the thickening agent is present in an amount of about 1 wt. %.

In some embodiments, a cosmetic composition of the present disclosure further comprises an emollient. Any emollient suitable for use in a cosmetic composition is contemplated. In some embodiments, the emollient is one or more of propylheptyl caprylate (CETIOL SENSOFT), C12-15 alkyl benzoate (LINCOL BAS), cetearyl isononanoate (LINCOL SN), butyrospermum parkii butter (BURRO DI KARITE), and combinations thereof. In some embodiments, the emollient is propylheptyl caprylate (CETIOL SENSOFT). In some embodiments, the emollient is a mixture of C12-15 alkyl benzoate (LINCOL BAS), cetearyl isononanoate (LINCOL SN) and butyrospermum parkii butter (BURRO DI KARITE). In some embodiments, the emollient is present in an amount of about 1 wt. % to about 20 wt. %, for example about 1 wt. %, about 1.25 wt. %, about 1.5 wt. %, about 1.75 wt. %, about 2 wt. %, about 2.25 wt. %, about 2.5 wt. %, about 2.75 wt. %, about 3 wt. %, about 3.25 wt. %, about 3.5 wt. %, about 3.75 wt. %, about 4 wt. %, about 4.25 wt. %, about 4.5 wt. %, about 4.75 wt. %, about 5 wt. %, about 5.25 wt. %, about 5.5 wt. %, about 5.75 wt. %, about 6 wt. %, about 6.25 wt. %, about 6.5 wt. %, about 6.75 wt. %, about 7 wt. %, about 7.25 wt. %, about 7.5 wt. %, about 7.75 wt. %, about 8 wt. %, about 8.25 wt. %, about 8.5 wt. %, about 8.75 wt. %, about 9 wt. %, about 9.25 wt. %, about 9.5 wt. %, about 9.75 wt. %, about 10 wt. %, about 10.25 wt. %, about 10.5 wt. %, about 10.75 wt. %, about 11 wt. %, about 11.25 wt. %, about 11.5 wt. %, about 11.75 wt. %, about 12 wt. %, about 12.25 wt. %, about 12.5 wt. %, about 12.75 wt. %, about 13 wt. %, about 13.25 wt. %, about 13.5 wt. %, about 13.75 wt. %, about 14 wt. %, about 14.25 wt. %, about 14.5 wt. %, about 14.75 wt. %, about 15 wt. %, about 15.25 wt. %, about 15.5 wt. %, about 15.75 wt. %, about 16 wt. %, about 16.25 wt. %, about 16.5 wt. %, about 16.75 wt. %, about 17 wt. %, about 17.25 wt. %, about 17.5 wt. %, about 17.75 wt. %, about 18 wt. %, about 18.25 wt. %, about 18.5 wt. %, about 18.75 wt. %, about 19 wt. %, about 19.25 wt. %, about 19.5 wt. %, about 19.75 wt. %, or about 20 wt. %. In some embodiments, the emollient is present in an amount of about 3 wt. %. In some embodiments, the emollient is present in an amount of about 10 wt. %.

In some embodiments, a cosmetic composition of the present disclosure further comprises a preservative. Any preservative suitable for use in a cosmetic composition is contemplated. In some embodiments, the preservative is one or more of benzoic acid, proprionic acid, salicylic acid, sorbic acid, biphenyl-2-ol, 4-hydroxybenzoic acid, 3-acetyl-6-methylpyran-2,4-(3H)-dione, formic acid, 3-3'-dibromo-4,4'-hexamethyulene-dioxydibenzamidineundec-10-enoic acid, 1,6-di-(4-amidinophenoxy)-n-hexane, cosmetically acceptable salts and/or esters of the foregoing, phenoxyethanol, ethylhexylglycerine, a mixture of phenoxyethanol and ethylhexylglycerine (EUXYL PE 9010), zinc pyrithione, inorganic sulphites, hydrogensulphites, chlorobutanol, thiomersal, phenylmercuric salts, hexetidine, 5-bromo-5-nitro-1,3-dioxane, bronopol, 2,4-dichlorobenzyl alcohol, triclocarban, 4-chloro-m-cresol, triclosan, 4-chloro-3,5-xylenol, 3,3'-bis-(1-hydroxymethyl-2,5-dioxoimidazolidin-4-yl)-1,1'-methylenediurea (also referred to as imidazolidinyl urea), poly-(1-hexamethylenebiguanide hydrochloride), 2-phenoxyethanol, hexamethylenetetramine(methenamine), methenamine 3-chloroallylochloride, 1-(4-chlorophenoxy)-1-(imidazol-1-yl)-3,3-dimethylbutan-2-one, 1,3-bis(hydroxymethyl)-5,5-dimethylimidazoline-2,4-dione, benzyl alcohol, 1-hydroxy-4-methyl-6-(2,4,4-trimethylpentyl)-2-pyridon, monoethanolamine salt of 1-hydroxy-4-methyl-6-(2,4,4-trimethylpentyl)-2-pyridon, 6,6-dibromo-4,4-dichloro-2,2'-methylenediphenol:bromochlorophen, 4-isopropyl-m-cresol, a mixture of 5-chloro-2-methylisothiazol-3-(2H)-one and 2-methylisothizaol-3-(2H)-one with magnesium chloride and magnesium nitrate, 2-benzyl-4-chlorophenol (also referred to as chlorophene), chlorhexidine and its digluconate, diacetate and dihydrochloride, 1-phenoxypropan-2-ol, alkyl (C12-22) trimethyl ammonium bromide and chloride, 4,4-dimethyl-1,3-oxazolidine, N-(hydroxymethyl)-N-(dihydroxymethyl-1,3-dioxo-2,5-imidazolinidyl-4)-N'-(hydroxymethyl)urea, glutaraldehyde, 5-ethyl-3,7-dioxa-1-azabicyclo[3.3.0]octane, 3-(p-chlorophenoxy)-propane-1,2-diol (also referred to as chlorphenesin), sodium hydroxymethylamino acetate, silver chloride deposited on titanium dioxide, benzethionium chloride, benzalkonium chloride, benzalkonium bromide, benzalkonium saccharinate, benzylhemiformal, iodopropynyl butyl-carbamate, methylisothiazolidinone, and combinations thereof. In some embodiments, the preservative is a mixture of phenoxyethanol and ethylhexylglycerine (EUXYL PE 9010). In some embodiments, the preservative is present in an amount of about 0.1 wt. % to about 5 wt. %, for example about 0.1 wt. %, about 0.2 wt. %, about 0.3 wt. %, about 0.4 wt. %, about 0.5 wt. %, about 0.6 wt. %, about 0.7 wt. %, about 0.8 wt. %, about 0.9 wt. %, about 1 wt. %, about 1.1 wt. %, about 1.2 wt. %, about 1.3 wt. %, about 1.4 wt. %, about 1.5 wt. %, about 1.6 wt. %, about 1.7 wt. %, about 1.8 wt. %, about 1.9 wt. %, about 2 wt. %, about 2.1 wt. %, about 2.2 wt. %, about 2.3 wt. %, about 2.4 wt. %, about 2.5 wt. %, about 2.6 wt. %, about 2.7 wt. %, about 2.8 wt. %, about 2.9 wt. %, about 3 wt. %, about 3.1 wt. %, about 3.2 wt. %, about 3.3 wt. %, about 3.4 wt. %, about 3.5 wt. %, about 3.6 wt. %, about 3.7 wt. %, about 3.8 wt. %, about 3.9 wt. %, about 4 wt. %, about 4.1 wt. %, about 4.2 wt. %, about 4.3 wt. %, about 4.4 wt. %, about 4.5 wt. %, about 4.6 wt. %, about 4.7 wt. %, about 4.8 wt. %, about 4.9 wt. %, or about 5 wt. %. In some embodiments, the thickening agent is present in an amount of about 0.5 wt. %. In some embodiments, the preservative is present in an amount of about 1 wt. %.

In some embodiments, a cosmetic composition of the present disclosure further comprises a fragrance. Any fragrance suitable for use in a cosmetic composition is contemplated. In some embodiments, the fragrance is PROFUMO FIOR D'ACQUA 85328. In some embodiments, the fragrance is present in an amount of about 0.05 wt. % to about 2 wt. %, for example about 0.05 wt. %, about 0.1 wt. %, about 0.15 wt. %, about 0.2 wt. %, about 0.25 wt. %, about 0.3 wt. %, about 0.35 wt. %, about 0.4 wt. %, about 0.45 wt. %, about 0.5 wt. %, about 0.55 wt. %, about 0.6 wt. %, about 0.65 wt. %, about 0.7 wt. %, about 0.75 wt. %, about 0.8 wt. %, about 0.85 wt. %, about 0.9 wt. %, about 0.95 wt. %, about 1 wt. %, about 1.1 wt. %, about 1.2 wt. %, about 1.3 wt. %, about 1.4 wt. %, about 1.5 wt. %, about 1.6 wt. %, about 1.7 wt. %, about 1.8 wt. %, about 1.9 wt. %, or about 2 wt. %. In some embodiments, the fragrance is present in an amount of about 0.2 wt. %. In some embodiments, the fragrance is present in an amount of about 0.5 wt. %. In some embodiments, the fragrance is present in an amount of about 0.7 wt. %.

In some embodiments, a cosmetic composition of the present disclosure further comprises an antioxidant. Any antioxidant suitable for use in a cosmetic composition is contemplated. In some embodiments, the antioxidant is one or more of dimethylmethoxy chromanol (LIPOCHROMAN); tocopherol; lecithin; ascorbyl palmitate; citric acid; a mixture of tocopherol, lecithin, ascorbyl palmitate, citric acid (APEROXIDE TLA); idebenone; and combinations thereof. In some embodiments, the antioxidant is dimethylmethoxy chromanol (LIPOCHROMAN). In some embodiments, the antioxidant is a mixture of dimethylmethoxy chromanol (LIPOCHROMAN) and ascorbyl palmitate. In some embodiments, the antioxidant is a mixture of tocopherol, lecithin, ascorbyl palmitate, citric acid (APEROXIDE TLA). In some embodiments, the antioxidant is present in an amount of about 0.005 wt. % to about 0.1 wt. %, for example about 0.005 wt. %, about 0.01 wt. %, about 0.015 wt. %, about 0.02 wt. %, about 0.025 wt. %, about 0.03 wt. %, about 0.035 wt. %, about 0.04 wt. %, about 0.045 wt. %, about 0.05 wt. %, about 0.055 wt. %, about 0.06 wt. %, about 0.065 wt. %, about 0.07 wt. %, about 0.075 wt. %, about 0.08 wt. %, about 0.085 wt. %, about 0.09 wt. %, about 0.095 wt. %, or about 0.1 wt. %. In some embodiments, the antioxidant is present in an amount of about 0.01 wt. %. In some embodiments, the antioxidant is present in an amount of about 0.02 wt. %. In some embodiments, the antioxidant is present in an amount of about 0.05 wt. %.

In some embodiments, a cosmetic composition of the present disclosure further comprises an emulsifier. Any emulsifier suitable for use in a cosmetic composition is contemplated. In some embodiments, the emulsifier is one or more of glyceryl stearate citrate (IMWITOR 372P), glyceryl stearate (CUTINA GMS/BERGABEST GS40/LINCOL GMS), behenyl alcohol (LANETTE 22/VEGARAL 22/AKEST AB/NAFOL 1822C), and combinations thereof. In some embodiments, the emulsifier is a mixture of glyceryl stearate citrate (IMWITOR 372P), glyceryl stearate (CUTINA GMS/BERGABEST GS40/LINCOL GMS), and behenyl alcohol (LANETTE 22/VEGARAL 22/AKEST AB/NAFOL 1822C). In some embodiments, the cosmetic composition does not include an emulsifier. In some embodiments, the emulsifier is present in an amount of about 0.5 wt. % to about 10 wt. %, for example about 0.5 wt. %, about 0.75 wt. %, about 1 wt. %, about 1.25 wt. %, about 1.5 wt. %, about 1.75 wt. %, about 2 wt. %, about 2.25 wt. %, about 2.5 wt. %, about 2.75 wt. %, about 3 wt. %, about 3.25 wt. %, about 3.5 wt. %, about 3.75 wt. %, about 4 wt. %, about 4.25 wt. %, about 4.5 wt. %, about 4.75 wt. %, about 5 wt. %, about 5.25 wt. %, about 5.5 wt. %, about 5.75 wt. %, about 6 wt. %, about 6.25 wt. %, about 6.5 wt. %, about 6.75 wt. %, about 7 wt. %, about 7.25 wt. %, about 7.5 wt. %, about 7.75 wt. %, about 8 wt. %, about 8.25 wt. %, about 8.5 wt. %, about 8.75 wt. %, about 9 wt. %, about 9.25 wt. %, about 9.5 wt. %, about 9.75 wt. %, or about 10 wt. %. In some embodiments, the emulsifier is present in an amount of about 5 wt. %.

In some embodiments, a cosmetic composition of the present disclosure further comprises a pH modifier. Any pH modifier suitable for use in a cosmetic composition is contemplated. In some embodiments, the pH modifier is sodium hydroxide. In some embodiments, the cosmetic composition does not include a pH modifier. In some embodiments, the pH modifier is present in an amount sufficient to bring the pH of the composition to about 5 to about 8, for example about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, or about 8.0. In some embodiments the pH is about 7 to about 7.15, for example about 7, about 7.01, about 7.02, bout 7.03, about 7.04, about 7.05 about 7.06, about 7.07, about 7.08 about 7.09, about 7.10, about 7.11 about 7.12, about 7.13, about 7.14, or about 7.15. In some embodiments, the pH is about 5.2 to about 5.5, for example about 5.2, about 5.28, about 5.3, about 5.32, about 5.35, about 5.4, about 5.41, or about 5.5. In some embodiments, the pH is about 5.8 to about 5.9, for example about 5.80, about 5.81, about 5.82, about 5.83, about 5.84, about 5.85, about 5.86, about 5.87, about 5.88, about 5.89, or about 5.90. In some embodiments, the pH modifier is present in an amount of about 0.05 wt. % to about 1 wt. %, for example about 0.05 wt. %, about 0.1 wt. %, about 0.15 wt. %, about 0.2 wt. %, about 0.25 wt. %, about 0.3 wt. %, about 0.35 wt. %, about 0.4 wt. %, about 0.45 wt. %, about 0.5 wt. %, about 0.55 wt. %, about 0.6 wt. %, about 0.65 wt. %, about 0.7 wt. %, about 0.75 wt. %, about 0.8 wt. %, about 0.85 wt. %, about 0.9 wt. %, about 0.95 wt. %, or about 1 wt. %. In some embodiments, the pH modifier is present in an amount of about 0.3 wt. %.

In some embodiments, a cosmetic composition of the present disclosure further comprises an adsorbing agent. Any adsorbing agent suitable for use in a cosmetic composition is contemplated. In some embodiments, the adsorbing agent is aluminum starch octenylsuccinate (DRY-FLO PC). In some embodiments, the cosmetic composition does not include an adsorbing agent. In some embodiments, the adsorbing agent is present in an amount of about 0.1 wt. % to about 5 wt. %, for example about 0.1 wt. %, about 0.2 wt. %, about 0.3 wt. %, about 0.4 wt. %, about 0.5 wt. %, about 0.6 wt. %, about 0.7 wt. %, about 0.8 wt. %, about 0.9 wt. %, about 1 wt. %, about 1.1 wt. %, about 1.2 wt. %, about 1.3 wt. %, about 1.4 wt. %, about 1.5 wt. %, about 1.6 wt. %, about 1.7 wt. %, about 1.8 wt. %, about 1.9 wt. %, about 2 wt. %, about 2.1 wt. %, about 2.2 wt. %, about 2.3 wt. %, about 2.4 wt. %, about 2.5 wt. %, about 2.6 wt. %, about 2.7 wt. %, about 2.8 wt. %, about 2.9 wt. %, about 3 wt. %, about 3.1 wt. %, about 3.2 wt. %, about 3.3 wt. %, about 3.4 wt. %, about 3.5 wt. %, about 3.6 wt. %, about 3.7 wt. %, about 3.8 wt. %, about 3.9 wt. %, about 4 wt. %, about 4.1 wt. %, about 4.2 wt. %, about 4.3 wt. %, about 4.4 wt. %, about 4.5 wt. %, about 4.6 wt. %, about 4.7 wt. %, about 4.8 wt. %, about 4.9 wt. %, or about 5 wt. %. In some embodiments, the adsorbing agent is present in an amount of about 1 wt. %.

In some embodiments, the cosmetic composition comprises or consists of: 0.815 wt. % to 4.080 wt. % of EPA, 0.285 wt. % to 1.425 wt. % of GLA, 0.1 wt. % of a sequestrant (e.g., disodium EDTA), 3 wt. % of a humectant (e.g., glycerine), 9 wt. % of a texturizing agent (e.g., a mixture of PEG-8-dimethicone, polysilicone-11, laureth-12, a crosspolymer of dimethicone and cetearyl dimethicone, silica, polyurethane and polymethylsilsesquioxane), 1 wt. % of a thickening agent (e.g., sodium polyacrylate), 3 wt. % of an emollient (e.g., propylheptyl caprylate), 1 wt. % of a preservative (e.g., phenoxyethanol and ethylhexylglycerine), fragrance (e.g., Profumo Fiori D'acqua) in an amount of 0.2 wt. %, 0.4 wt. % or 0.7 wt. %, 0.01 wt. % of an antioxidant (e.g., dimethylmethoxy chromanol), and balance solvent (e.g., water), wherein the EPA and GLA are present in a weight-to-weight ratio of about 4:1. In one such embodiment, the EPA and GLA are present in amounts of 0.815 wt. % and 0.285 wt. %, respectively, and the fragrance is present in an amount of 0.2 wt. %. In another such embodiment, the EPA and GLA are present in amounts of 1.631 wt. % and 0.57 wt. %, respectively, and the fragrance is present in an amount of 0.4 wt. %. In yet another such embodiment, the EPA and GLA are present in amounts of 4.08 wt. % and 1.425 wt. %, respectively, and the fragrance is present in an amount of 0.7 wt. %.

In some embodiments, the cosmetic composition comprises or consists of: 0.815 wt. % to 4.08 wt. % of EPA, 0.285 wt. % to 1.425 wt. % of GLA, 0.1 wt. % of a sequestrant (e.g., disodium EDTA), 3 wt. % of a humectant (e.g., glycerine), 8 wt. % of a texturizing agent (e.g., a mixture of PEG-8-dimethicone, polysilicone-11, laureth-12, a crosspolymer of dimethicone and cetearyl dimethicone, and silica), 1 wt. % of a thickening agent (e.g., polymeric sulphonic acid), 3 wt. % of an emollient (e.g., propylheptyl caprylate), 1 wt. % of a preservative (e.g., phenoxyethanol and ethylhexylglycerine), fragrance (e.g., Profumo Fiori D'acqua) in an amount of 0.2 wt. %, 0.4 wt. % or 0.7 wt. %, 0.05 wt. % of an antioxidant (e.g., a mixture of tocopherol, lecithin, ascorbyl palmitate and citric acid), and balance solvent (e.g., water), wherein the EPA and GLA are present in a weight-to-weight ratio of about 4:1. In one such embodiment, the EPA and GLA are present in amounts of 0.815 wt. % and 0.285 wt. %, respectively, and the fragrance is present in an amount of 0.2 wt. %. In another such embodiment, the EPA and GLA are present in amounts of 1.631 wt. % and 0.57 wt. %, respectively, and the fragrance is present in an amount of 0.4 wt. %. In yet another such embodiment, the EPA and GLA are present in amounts of 4.08 wt. % and 1.425 wt. %, respectively, and the fragrance is present in an amount of 0.7 wt. %.

In some embodiments, the cosmetic composition comprises or consists of: 0.815 wt. % to 4.08 wt. % of EPA, 0.285 wt. % to 1.425 wt. % of GLA, 0.1 wt. % of a sequestrant (e.g., disodium EDTA), 3 wt. % of a humectant (e.g., glycerine), 0.5 wt. % of a thickening agent (e.g., sodium polyacrylate), 5 wt. % of an emulsifier (e.g., a mixture of glyceryl stearate citrate, glyceryl stearate and behenyl alcohol), 10 wt. % of an emollient (e.g., a mixture of C12-15 alkyl benzoate, cetearyl isononanoate and butyrospermum parkii butter), 1 wt. % of a preservative (e.g., phenoxyethanol and ethylhexylglycerine), 0.7 wt. % of fragrance (e.g., Profumo Fiori D'acqua), 0.02 wt. % of an antioxidant (e.g., a mixture of dimethylmethoxy chromanol and ascorbyl palmitate), 0.3 wt. % of a pH modifier (e.g., sodium hydroxide), 1 wt. % of an adsorbing agent (e.g., aluminum starch octenylsuccinate), and balance solvent (e.g., water), wherein the EPA and GLA are present in a weight-to-weight ratio of about 4:1. In one such embodiment, the EPA and GLA are present in amounts of 0.815 wt. % and 0.285 wt. %. In another such embodiment, the EPA and GLA are present in amounts of 1.631 wt. % and 0.57 wt. %, respectively. In yet another such embodiment, the EPA and GLA are present in amounts of 4.08 wt. % and 1.425 wt. %, respectively. In some embodiments, the cosmetic composition is free of unpleasant odors (e.g., has a cosmetically acceptable odor).

Cosmetic compositions of the present disclosure can be made according to any suitable method known in the art. Typically, the solvents, humectants, and sequestrants are added to a suitably sized main vessel and heated to a temperature of about 70° C. to about 75° C. While heating, thickening agent is added and homogenized at high speed for an effective time, typically about 15 minutes. In a second vessel, the emulsifiers and emollients are melted together (e.g., heated to about 70° C. to about 75° C.), and the melted mixture is added to the main vessel. The main vessel is then homogenized and cooled to about 25° C. If used, the adsorbing agent is next heated in a third vessel to about 50° C. and added to the main vessel. The preservative system is then heated to 35° C. and then added to the main vessel. Next, fragrances and antioxidants are combined and then added to the main vessel. The pH modifier is then added to the main vessel. The EPA and GLA are then combined in a separate vessel before being added to the main vessel.

Cosmetic compositions of the present disclosure may be used as any type of cosmetic product including, for example, topical compositions (e.g., creams, powders, balms, ointments, etc.), lotions, and the like. In some embodiments, the cosmetic composition is a topical formulation.

In one embodiment, the present disclosure provides a method of treating and/or preventing wrinkles in skin of a subject. In some embodiments, the method comprises topically administering a composition according to the present disclosure to at least a portion of skin of the subject.

In one embodiment, the present disclosure provides a method of treating and/or preventing seborrheic dermatitis in skin of a subject. In some embodiments, the method comprises topically administering a composition according to the present disclosure to at least a portion of the skin of the subject.

In one embodiment, the present disclosure provides a method of treating and/or preventing a skin disease or disorder in a subject. In some embodiments, the method comprises topically administering a composition according to the present disclosure to at least a portion of the skin of the subject.

In some embodiments, a method of treating and/or preventing wrinkles comprises topically administering to skin of a subject an effective amount of a cosmetic composition as disclosed herein. In some embodiments, the cosmetic composition is applied once per day, twice per day, three times per day, four times per day, or more than four times per day. In some embodiments, the cosmetic composition is topically applied for at least one week, at least 2 weeks, at least 3 weeks, at least 4 weeks, at least 5 weeks, at least 6 weeks, at least 7 weeks, at least 8 weeks, at least 9 weeks, at least 10 weeks, at least 11 weeks, at least 12 weeks, at least 13 weeks, at least 14 weeks, at least 15 weeks, at least 16 weeks, at least 17 weeks, at least 18 weeks, at least 19 weeks, at least 20 weeks, at least 26 weeks, at least 52 weeks, at least 2 years, at least 3 years, at least 4 years, at least 5 years, at least 6 years, at least 7 years, at least 8 years, at least 9 years, or at least 10 years.

In one embodiment, the present disclosure provides a method of treating or preventing acne associated with *P. acnes* in a subject in need thereof. In one embodiment, the method comprises administering to the subject a cosmetic composition as disclosed herein. In one embodiment, the cosmetic composition comprises a therapeutically effective amount of EPA and GLA. In one embodiment, the cosmetic composition comprises about 0.1 wt. % to about 10 wt. % of a combination of an EPA component and a GLA component. In some embodiments, the cosmetic composition comprises the EPA and the GLA components in a ratio of 4:1. In some embodiments, the EPA component comprises at least 95% pure EPA free acid. In some embodiments, the GLA component comprises at least 70% GLA free acid.

In one embodiment, the present disclosure provides a method of inhibiting *P. acnes* including, for example, its growth, colonization and/or infection, in a subject in need thereof. In one embodiment, the method comprises contacting *P. acnes* with a composition as disclosed herein. In one embodiment, the composition comprises one or more of EPA and GLA. In one embodiment, the composition comprises from about 0.1 wt. % to about 10 wt. % of a combination of EPA and GLA. In some embodiments, the cosmetic composition comprises the EPA and the GLA components in a ratio of 4:1. In some embodiments, the EPA component comprises at least 95% pure EPA free acid. In some embodiments, the GLA component comprises at least 70% GLA free acid.

In some embodiments the composition comprises a mixture of an EPA component and a GLA component. In some embodiments, the EPA component comprises at least 95% pure EPA free acid, for example 95%, at least 96%, at least 97%, at least 98%, at least 99%, or 100% EPA free acid, while the GLA component comprises at least 70% GLA free acid, for example at least 70%, at least 70.2%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, or at least 89% GLA free acid. In some embodiments, the composition comprises the EPA and the GLA components in a ratio of 4:1. In some embodiments, the composition comprising an EPA component and a GLA component (e.g., in a ratio of about 4:1) is admixed with an anti-acne therapy in a cosmetically useful formulation. In one embodiment, the anti-acne therapy comprises salicylic acid and/or benzoyl peroxide.

EXAMPLES

Example 1

Topical Formulation "A"

A topical composition was prepared by combining the components listed in Table 1 according to the method described above. EPA free fatty acid was provided in the form of a composition comprising 98.1 wt. % EPA free acid GLA free fatty acid was provided in the form of a composition comprising 70.2 wt. % GLA free acid. Values for EPA and GLA reflect the purity of the composition from which each was added. The final formulation had the composition shown in Table 1, below, as follows;

TABLE 1

Composition of Topical Formulation "A"

| Ingredient | Chemical Name | Function | Low (wt. %) | Medium (wt. %) | High (wt. %) |
|---|---|---|---|---|---|
| Purified Water | Water | Solvent | 81.590 | 80.289 | 76.685 |
| Trilon B | Disodium EDTA | Sequestrant | 0.100 | 0.100 | 0.100 |
| Glycerine Veg. PH EUR 99.5% | Glcerin | Humectant | 3.000 | 3.000 | 3.000 |
| Silwax WS | PEG-8-Dimethicone | Texturizing Agent | 2.000 | 2.000 | 2.000 |
| Cosmedia SP | Sodium Polyacrylate | Thickening Agent | 1.000 | 1.000 | 1.000 |
| Cetiol Sensoft | Propylheptyl Caprylate | Emollient | 3.000 | 3.000 | 3.000 |
| Gransil EPS | Polysilicone-11 & Laureth 12 | Texturizing Agent | 2.000 | 2.000 | 2.000 |
| Velvesil DM | Dimethicone & Cetearyl Dimethicone Crosspolymer | Texturizing Agent | 2.000 | 2.000 | 2.000 |
| Cosmedia Silc | Silica | Texturizing Agent | 1.500 | 1.500 | 1.500 |
| Granpowder USQ | Polyurethane and Polymethylsilsesquioxane | Texturizing Agent | 1.500 | 1.500 | 1.500 |
| Euxyl PE 9010 | Phenoxyethanol & Ethylhexylglycerin | Preservative | 1.000 | 1.000 | 1.000 |
| Profumo Fiori D'acqua 85328 | | Fragrance | 0.200 | 0.400 | 0.700 |
| Lipochroman | Dimethylmethoxy Chromanol | Antioxidant | 0.010 | 0.010 | 0.010 |
| EPA FFA | Eicosapentaenoic Acid | Active | 0.815 | 1.631 | 4.080 |
| GLA FFA | Gamma Linolenic Acid | Active | 0.285 | 0.570 | 1.425 |

Example 2

Topical Formulation "B"

A topical composition was prepared by combining the components listed in Table 2 according to the method described above. EPA free fatty acid was added in the form of a composition comprising 98.1 wt. % EPA free acid GLA free fatty acid was added in the form of a composition comprising 70.2 wt. % GLA free acid. Values for EPA and GLA reflect the purity of the composition from which each was added. The final formulation had the composition shown in Table 2, below.

TABLE 2

Composition of Topical Formulation "B"

| Ingredient | Chemical Name | Function | Low (wt. %) | Medium (wt. %) | High (wt. %) |
|---|---|---|---|---|---|
| Purified Water | Water | Solvent | 82.550 | 81.249 | 77.645 |
| Trilon B | Disodium EDTA | Sequestrant | 0.100 | 0.100 | 0.100 |
| Glycerine Veg. PH EUR 99.5% | Glycerin | Humectant | 3.000 | 3.000 | 3.000 |
| Silwax WS | PEG-8-Dimethicone | Texturizing Agent | 2.000 | 2.000 | 2.000 |
| Aristoflex AVC | Polymeric Sulphonic Acid | Thickening Agent | 1.000 | 1.000 | 1.000 |
| Cetiol Sensoft | Propylheptyl Caprylate | Emollient | 3.000 | 3.000 | 3.000 |
| Gransil EPS | Polysilicone-11 & Laureth 12 | Texturizing Agent | 2.000 | 2.000 | 2.000 |
| Velvesil DM | Dimethicone & Cetearyl Dimethicone Crosspolymer | Texturizing Agent | 2.000 | 2.000 | 2.000 |
| Cosmedia Silc | Silica | Texturizing Agent | 2.000 | 2.000 | 2.000 |
| Euxyl PE 9010 | Phenoxyethanol & Ethylhexylglycerin | Preservative | 1.000 | 1.000 | 1.000 |
| Profumo Fiori Dacqua 85328 | | Fragrance | 0.200 | 0.400 | 0.700 |
| Aperoxide TLA | Tocopherol, Lecithin, Ascorbyl Palmitate and Citric Acid | Antioxidant | 0.050 | 0.050 | 0.050 |
| EPA FFA | Eicosapentaenoic Acid | Active | 0.815 | 1.631 | 4.080 |

TABLE 2-continued

Composition of Topical Formulation "B"

| Ingredient | Chemical Name | Function | Weight Percent (wt. %) | | |
|---|---|---|---|---|---|
| | | | Low | Medium | High |
| GLA FFA | Gamma Linolenic Acid | Active | 0.285 | 0.570 | 1.425 |

Example 3

Topical Formulation "C"

A topical composition was prepared was prepared by combining water, glycerine and disodium EDTA in a main vessel and heating to 70-70° C. While the mixture was heating, the thickening agent (sodium polyacrylate) was added and homogenized at high speed for 15 minutes. In a secondary vessel, the emulsifiers and emollients were combined and heated to 70-75° C. The melted emulsifiers and emollients were then added to the main vessel and homogenized for 15 minutes. The mixture was then cooled to 25° C. The adsorbing agent was heated to 50° C. and added to the main vessel. The preservative was then heated to 35° C. before being added to the main vessel. The fragrance and antioxidants were combined and then added to the main vessel. The pH modifier was added to the main vessel, followed by a mixture of the EPA and GLA.

The final formulation had the composition shown in Table 3, below.

Surprisingly, topical formulation C was devoid of the unpleasant odor commonly associated with compositions comprising fatty acids in free acid form.

Example 4

Properties of Formulations A to C

The color, pH, and viscosity (20° C.) of Formulations A to C were determined according to standard methods, as shown in Table 4, below.

TABLE 4

Properties of Formulations A to C.

| Formulation | Low/Medium/High | Color | pH | Viscosity (20° C.) |
|---|---|---|---|---|
| A | Low | Off-white | 5.83 | 22,000 mPas |
| | Medium | Off-white | 5.84 | 21,800 mPas |
| | High | Off-white, slightly yellow | 5.81 | 18,000 mPas |

TABLE 3

Composition of Topical Formula "C"

| Ingredient | Chemical Name | Function | Weight Percent (wt. %) | | |
|---|---|---|---|---|---|
| | | | Low | Medium | High |
| Purified Water | Water | Solvent | 77.280 | 76.179 | 72.875 |
| Trilon B | Disodium EDTA | Sequestrant | 0.100 | 0.100 | 0.100 |
| Glycerine Veg. PH EUR 99.5% | Glycerin | Humectant | 3.000 | 3.000 | 3.000 |
| Cosmedia SP | Sodium Polyacrylate | Thickening Agent | 0.500 | 0.500 | 0.500 |
| Imwitor 372P | Glyceryl Stearate Citrate | Emulsifier | 2.000 | 2.000 | 2.000 |
| Lincol BAS | C12-15 Alkyl Benzoate | Emollient | 3.000 | 3.000 | 3.000 |
| Lincol SN | Cetearyl Isononanoate | Emollient | 5.000 | 5.000 | 5.000 |
| Cutina GMS/Bergabest GS40/Lincol GMS | Glyceryl Stearate | Emulsifier | 2.000 | 2.000 | 2.000 |
| Lanette 22/Vegarol 22/Akest AB/Nafol 1822C | Behenyl Alcohol | Co-Emulsifier | 1.000 | 1.000 | 1.000 |
| Burro Di KARITE | Butyrospermum Parkii Butter | Emollient | 2.000 | 2.000 | 2.000 |
| Dry-Flo PC | Aluminum Starch Octenylsuccinate | Adsorbing Agent | 1.000 | 1.000 | 1.000 |
| Euxyl PE 9010 | Phenoxyethanol & Ethylhexylglycerin | Preservative System | 1.000 | 1.000 | 1.000 |
| Profumo Fiori Dacqua 85328 | Fragrance | Odour Masking | 0.700 | 0.700 | 0.700 |
| Lipochroman | Dimethylmethoxy Chromanol | Antioxidant | 0.010 | 0.010 | 0.010 |
| Ascorbyl Palmitate | Ascorbyl Palmitate | Antioxidant | 0.010 | 0.010 | 0.010 |
| Sodium Hydroxide | Sodium Hydroxide | pH Modifier | 0.300 | 0.300 | 0.300 |
| EPA FFA | Eicosapentaenoic Acid | Active | 0.815 | 1.631 | 4.080 |
| GLA FFA | Gamma Linolenic Acid | Active | 0.285 | 0.570 | 1.425 |

TABLE 4-continued

Properties of Formulations A to C.

| Formulation | Low/Medium/High | Color | pH | Viscosity (20° C.) |
|---|---|---|---|---|
| B | Low | Off-white | 5.35 | 10,200 mPas |
|   | Medium | Off-white | 5.32 | 10,300 mPas |
|   | High | Off-white, slightly yellow | 5.28 | 11,200 mPas |
| C | Low | Off-white | 7.10 | 33,000 mPas |
|   | Medium | Ivory-white | 7.12 | 32,100 mPas |
|   | High | Ivory | 7.10 | 30,600 mPas |

Example 5

Antioxidant Capabilities of Disclosed Compositions

A study to determine the antioxidant capabilities of skin after application of Formulations A-C of Examples 1-3 includes 16 male and female subjects, each age 35 to 50 years. Chromameter measurements are performed on the volar forearm to define each subject's individual typography angle ("ITA°"). Six small spots are then exposed to ITA°-dependent doses of UVA/UVB radiation. After 24 hours, each subject's minimal erythemal dose ("MED") is assessed.

Four test areas are defined on a non-UV-exposed portion of each subject's volar forearm. One test area serves as a negative control, while a composition of each of Formulations A-C of Examples 1-3 is applied to the other three test areas once per day for three days. Two hours after the application on day 3, each test area receives twice the MED dose of UVA/UVB light. After a 24-hour waiting period, chromametric measurements are obtained, and biopsies from each of the three test areas and the negative control area are collected and analyzed.

Analysis of the skin biopsies includes determining the content of at least three markers: matrix metalloproteinase-1 ("MMP-1"), malondialdehyde ("MDA") and interleukin-8 ("IL-8"). Differences between the treated test areas and the negative control are determined using standard statistical methods.

Example 6

Effect of Disclosed Compositions on Biophysical Properties of Skin

A study to determine the effect of Formulations A-C of Examples 1-3 includes 28 male and female subjects, each age 35 to 50 years. Chromameter measurements are performed on the volar forearm to define each subject's individual typography angle ("ITA°"). Six small spots are then exposed to ITA°-dependent doses of UVA/UVB radiation. After 24 hours, each subject's minimal erythemal dose ("MED") is assessed. Baseline biophysical measurements are also obtained at this time, including epidermal thickness (e.g., by a Vivascope or similar instrument), skin elasticity (e.g., by a Cutometer or similar instrument), skin hydration (e.g., by a Corneometer or similar instrument), and skin roughness/fine line assessment/3-dimensional structure (e.g., by use of a Phase-shifted Rapid In vivo Measurement Of human Skin—"PRIMOS"—or a similar instrument).

Each subject then applies each of Formulations A-C of Examples 1-3 twice daily for 12 weeks. During the 12-week test period, each subject visits a test facility to be exposed to suberythemal irradiation by a defined solar simulator.

At the end of the 12-week test period, biophysical measurements as described above are obtained, and skin biopsies are procured. Epidermal thickness, papillary index, and collagen fiber networks are assessed, along with determination of COX-2 and procollagen-1 levels. Differences between the test areas and the negative control are determined using standard statistical methods.

Example 7

Effect of Formulations A to C on Skin Roughness Induced by Suberythemal UV Irratiation A study to determine the efficacy of Formulations A to C to prevent drying out and roughening of the skin during repeated suberythemal irradiation with a sun simulator that emits UVB and UVA radiation is performed. The subjects include fourteen male and female humans each having type II or type III skin.

During the week before treatment, the minimum erythemal dose (MED) for each subject is determined by irradiating six small spots on the subject's volar forearm with a sun simulator (UVASPOT 1000, Horde). Dose increments are increased by 25% to detect the MED, which is read 16-24 hours after irradiation.

Each subject's volar forearm area is divided into four 4 cm by 5 cm test areas. One area serves as an untreated, irradiated control. A second area is not treated and is not irradiated to serve as a second control.

On days 1 to 12, product applications are performed by the subjects with the exception that applications performed in the morning of the days with an appointment at the study site are performed by trained personnel. On each test area, 2 mg per $cm^2$ of one of Formulations A to C is applied by the trained personnel. The subjects are similarly trained by a technician to apply the same 2 mg per $cm^2$ dose. Fifteen minutes after the Formulation is applied, irradiation on the 3 irradiated test areas is performed with the sun simulator. On days 1 and 3, 0.6 MED are irradiated. On days 5 and 8, 0.75 MED are irradiated, and on days 10 and 12, 1 MED is irradiated. In cases of visible erythema on one or more test areas, the irradiation is skipped for the subject on all test areas until no more erythema is apparent.

Measurements of skin roughness is performed at baseline and on day 12. Measurements are taken before test product application. Using Phase-shifted Rapid In vivo Measurement Of human Skin (PRIMOS), a three-dimensional surface structure of the investigated skin site is captured. The measuring principle is based on digital fringe projection. The fringes that are projected are detected with a CCD camera. The three-dimensional structure is then calculated from the position of the fringes in combination with the gray values of each pixel.

From the captured three-dimensional structure, roughness parameters are calculated. The parameters Rz and Ra are chosen, representing mainly the rough structure (Rz) and the finer skin structure (Ra). An increase or decrease in the roughness parameters corresponded to an increase or decrease in the degree of skin roughness.

Measurements of skin moisture (KAP) are performed at baseline and on days 3, 5, 10 and 12. Measurements are taken before test product application. The evaluation is performed with a Corneometer (CM 825) and is based on the capacitance measuring principle—that is, the distinctly different dielectric constants of water and other substances. This method is described in the literature in detail and is generally accepted as a reproducible and reliable parameter for skin hydration measurements. As standard procedure, measurements are repeated 5 times. Mean values are taken from the 3 middle measuring points; the highest and lowest values are dismissed. By this approach more stable values were achieved.

For all parameters, appropriate statistical methods are used to analyze the differences between the test products and the untreated control.

Example 8

Reducing Skin Roughness as a Marker for Anti-Wrinkle Effect

A study to determine the efficacy of a composition of the present disclosure to reduce skin roughness (as a marker for reducing and/or preventing wrinkles) was performed.

During the week leading up to initial treatment (Days −7 to −1), subjects were informed about the study and gave written consent. The suitability of each subject was evaluated according to inclusion/exclusion criteria shown in Table 5, below. Subjects that fulfilled the inclusion/exclusion criteria were enrolled into the study.

TABLE 5

Inclusion and Exclusion Criteria.

| Inclusion Criteria | Exclusion Criteria | |
|---|---|---|
| Male and/or female | Pregnancy or lactation | Application of leave-on |
| From 18 to 65 years of age | Drug addicts, alcoholics | cosmetics (e.g. creams, |
| Written Informed Consent | AIDS or infectious hepatitis | lotions, sun screen lotions, |
| Form to participate in the | if known to the subject | oil bath, creamy shower) at |
| study | Conditions which exclude a | the test area within the last |
| Willingness to actively | participation or might | 3 days prior to the start of |
| participate in the study and | influence the test | the study |
| to come to the scheduled | reaction/evaluation | Moles, tattoos, scars, |
| visits | One of the following serious | irritated skin, hairs etc. at |
| Willingness to discontinue | illnesses that might require | the test area that could |
| the use of detergents (e.g. | regular systemic | influence the investigation |
| soaps) and cosmetic | medication: insulin- | Systemic therapy with |
| products (e.g. creams, | dependent diabetes, cancer | immunosuppressive drugs |
| moisturizers) in the | One of the following serious | (e.g. corticosteroids) |
| treatment areas throughout | illnesses, if not medicated: | and/or antihistamines |
| the course of the study | asthma, hypertension | within the last 7 days |
| Willingness to avoid any | Electronic implant (e.g. | Systemic therapy with anti- |
| exposure of the test area to | pace maker, insulin pump, | phlogistic agents or |
| artificial or natural UV light | hearing aid, and the like) | analgetics (e.g. diclophenac |
| throughout the course of the | that cannot be removed | or celecoxib) within the last |
| study | during irradiation | 3 days (except for minor |
| Skin phototype II or III | Active skin disease at test | pain relief medicine, like |
| (according to Fitzpatrick) | area | acetylsalicylic acid or |
| ITA° > 28 in the test area | Documented allergies to | paracetamol) |
| Uniform skin color and no | cosmetic products | Usage of medication with |
| erythema or dark | Medical history of | known photo-toxic and/or |
| pigmentation in the test | dysplastic nevi or | photo-sensitizing potential |
| area | melanoma | (e.g. Hypericum |
| | Medical history of abnormal | perforatum, antibiotics, |
| | response to sunlight | blood pressure regulating |
| | Regular use of tanning beds | agents) within the last 14 |
| | Sun exposition, UV- | days |
| | therapy, artificial tanning | Participation or being in a |
| | within the last 4 weeks, or | waiting period of 2 months |
| | irregularly tanned skin in | after participation in |
| | the test area | cosmetic and/or |
| | | pharmaceutical UV studies |

Chromameter measurements were performed on the volar forearms to determine ITA° values for each subject. Briefly, six small spots were irradiated on the forearms between the prospective test areas with the solar simulator, each successive spot having an incremental dose of 25%, in order to detect the individual Minimal Erythemal Dose (MED) of the subjects. The MED was read 16 to 24 hours after irradiation.

On Day 1, subjects were acclimatized for 30 minutes. Measurements of skin roughness were performed after skin hydration was measured. Test products were applied to each subject by a trained technician as follows. DS101A (vehicle placebo) was applied to a first test area, DS101C (a 5% cream composition consistent with the present disclosure with a formulation as shown in Table 6 below) was applied to a second test area, while two additional test areas remained untreated. After 15 minutes, the two treated test areas and one untreated test area were irradiated with 0.6 MED. The fourth (untreated) test area was not irradiated. Subjects repeated application of DS101A and DS101C in the evening according to instructions of the technician.

TABLE 6

DS101C Test Composition Formulation.

| Component | INCI/Chemical Name | DS101C Amount (wt. %) |
|---|---|---|
| EPA | Eicosapentaenoic acid | 4.000 |
| GLA | Gamma Linolenic acid | 1.000 |

TABLE 6-continued

DS101C Test Composition Formulation.

| Component | INCI/Chemical Name | DS101C Amount (wt. %) |
|---|---|---|
| Purified Water | Water | qs |
| Disodium EDTA (Trilon B) | Disodium EDTA | 0.100 |
| Glycerine Veg. PH EUR 99.5% | Glycerine | 3.000 |

TABLE 6-continued

DS101C Test Composition Formulation.

| Component | INCI/Chemical Name | DS101C Amount (wt. %) |
|---|---|---|
| Cosmedia SP | Sodium Polyacrylate | 0.500 |
| Imwitor 372P | Glyceryl Stearate Citrate | 2.000 |
| Lincol BAS | C12-15 Alkyl Benzoate | 3.000 |
| Lincol SN | Cetearyl Isononanoate | 5.000 |
| Lincol GMS | Glyceryl Stearate | 2.000 |
| Nafol 1822C | Behenyl Alcohol | 1.000 |
| Burro Di Karite | Butyrospermum Parkii Butter | 2.000 |
| Dry-Flo PC | Aluminum Starch Octenylsuccinate | 1.000 |
| Euxyl PE 9010 | Phenoxyethanol & Ethylhexylglycerin | 1.000 |
| Profumo Fiori D'acqua 85328 | Fragrance | 0.700 |
| Lipochroman | Dimethylmethoxy Chromanol | 0.010 |
| Ascorbyl Palmitate | Ascorbyl Palmitate | 0.010 |
| Sodium Hydroxide (30%) | Sodium Hydroxide/Water | 0.300 |

On Day 3, subjects we acclimatized for 30 minutes. Measurements of skin hydration were performed. Product application was performed by a trained technician as described for Day 1. After 15 minutes, the two treated test areas and one untreated test area were irradiated with 0.6 MED. The fourth (untreated) test area was not irradiated. Subjects repeated application of DS101A and DS101C in the evening according to instructions of the technician.

On Day 5, subjects we acclimatized for 30 minutes. Measurements of skin hydration were performed. Product application was performed by a trained technician as described for Day 1. After 15 minutes, the two treated test areas and one untreated test area were irradiated with 0.75 MED. The fourth (untreated) test area was not irradiated. Subjects repeated application of DS101A and DS101C in the evening according to instructions of the technician.

On Day 8, subjects we acclimatized for 30 minutes. Measurements of skin hydration were performed. Product application was performed by a trained technician as described for Day 1. After 15 minutes, the two treated test areas and one untreated test area were irradiated with 0.75 MED. The fourth (untreated) test area was not irradiated. Subjects repeated application of DS101A and DS101C in the evening according to instructions of the technician.

On Day 10, subjects we acclimatized for 30 minutes. Measurements of skin hydration were performed. Product application was performed by a trained technician as described for Day 1. After 15 minutes, the two treated test areas and one untreated test area were irradiated with 1 MED. The fourth (untreated) test area was not irradiated. Subjects repeated application of DS101A and DS101C in the evening according to instructions of the technician.

On Day 12, subjects we acclimatized for 30 minutes. Measurements of skin hydration were performed. Product application was performed by a trained technician as described for Day 1. After 15 minutes, the two treated test areas and one untreated test area were irradiated with 1 MED. The fourth (untreated) test area was not irradiated. Subjects repeated application of DS101A and DS101C in the evening according to instructions of the technician.

On each of Days 2, 4, 6, 7, 9, 11, 13 and 14, subjects applied DS101A and DS101C to test areas twice daily as instructed.

On Day 15, subjects were acclimatized for 30 minutes. Skin hydration was measured, followed by skin roughness.

In case of visible erythema on one or more test areas, the subject's test areas were not irradiated until erythema was no longer visible.

A summary of the test schedule is provided below.

| | Test Schedule | | | | | | | | | | | | | |
|---|---|---|---|---|---|---|---|---|---|---|---|---|---|---|
| | Day | | | | | | | | | | | | | |
| Actions | −7 to −1 | 1 | 2 | 3 | 4 | 5 | 6 | 7 | 8 | 10 | 11 | 12 | 13 | 14 | 15 |
| MED Determination | X | | | | | | | | | | | | | | |
| Skin Hydration (Capacitance) | | X | | X | | X | | | X | X | | X | | | X |
| Skin Surface Profile | | X | | | | | | | | | | | | | X |
| Application of Test Materials twice daily | | X | X | X | X | X | X | X | X | X | X | X | X | X | |
| UV-irradiation | | X | | X | | X | | | X | X | | X | | | |

Skin Hydration Measurement

Measurement of stratum corneum hydration was performed by the electrical capacitance method with the Corneometer.CM 825 (Courage & Khazaka, Cologne, Germany). The measuring principle is based on changes in the capacitance of the measuring head, functioning as a condensator. Between the conductors consisting of gold, an electrical field is built. By these means, the dielectricity of the upper skin layer is measured. Because the dielectricity varies as a function of the skin's water content, the stratum corneum hydration can be determined.

As a rough guide, values lower than 30 instrumental units (i.u.) usually represent very dry skin, while values between 30 and 40 i.u. typically indicate dry skin. The range of 40 i.u. and higher generally indicates normally hydrated skin. An increase in Corneometer values over time (e.g., at one visit compared to an earlier visit), therefore, shows a skin-moisturizing effect.

Skin Surface Profile, Single Measurement

Using Phase-shifted Rapid In vivo Measurement Of human Skin (PRIMOS), the three-dimensional surface structure of the investigated skin site was captured. The measuring principle was based on digital fringe projection. The fringes that are projected under the so-called triangulation angle onto the surface of the measured target with a sinus-like intensity of brightness were detected with a CCD camera. The three-dimensional structure was calculated from the position of the fringes in combination with the grey values of each pixel.

From the captured three-dimensional structure, roughness parameters were calculated. The parameters Rz were Ra are chosen, representing mainly the rough structure (Rz) and the finer skin structure (Ra). An increase or decrease in the roughness parameters corresponded to an increase or decrease in the degree of skin roughness.

UV-Irradiation, Irradiation of UVB and UVA

A sun simulator (UVA Spot 1000, Filter H2, Hönle, Germany) was used to irradiate the test areas with the requested irradiation intensity on the test areas. The test areas may be irradiated at the same time.

Results

As shown in FIG. 1, the EPA/GLA test product reduced UV-induced skin roughness more effectively than placebo. Data shown is Day 15 compared to Day 1.

Example 9

Anti-Acne Effects

Materials and Methods
Test Compounds and Bacterial Cultures

All bacterial culture media and reagents were purchased from Sigma-Aldrich Ltd unless stated otherwise.

A stock solutions of salicylic acid ("SA") at 50 mg/mL, and stock solutions of azelaic acid ("AZA"), >95% eicosapentaenoic acid ("EPA"), >95% gamma-linolenic acid ("GLA"), and lower-purity gamma-linolenic acid ("GLA 70%"), each at 100 mg/mL, were prepared in ethanol. Stock solutions of benzoyl peroxide ("BPO," 50 mg/mL) and furosemide ("FUS," 20 mg/mL) were prepared in DMSO and distilled water, respectively. Neomycin ("NEO") was obtained and used as a 10 mg/mL solution in sterile saline. *P. acnes* NCTC737 was obtained from the National Collection of Type Cultures (Porton Down, UK).

Minimum inhibitory (MIC) and bactericidal (MBC) concentration determinations MICs and MBCs were determined against *P. acnes* by broth micro-dilution according to protocol M11-A5 published by the Clinical and Laboratory Standards Institute (CLSI, 2001). Briefly, doubling dilutions of the test compounds were prepared in sterile 96-well plates up to 4096 mg/L for AZA, EPA, GLA, GLA 70%, BPO, and SA; 512 mg/L for NEO and 32 mg/L for FUS. The *P. acnes* inoculum was prepared in 3 mL supplemented *brucella* broth (SBB) by re-suspending colonies from a supplemented *brucella* agar (SBA) plate that had been grown anaerobically (10% $CO_2$, 10% $H_2$, 80% $N_2$) for ca. 72 h at 37° C. (A85 Workstation; Don Whitley Scientific Ltd., Shipley, UK). Absorbance readings (A600) for the bacterial suspensions were determined and fresh media was used to adjust the inoculums to $1\times10^7$ CFU/mL.

Inoculum sizes were confirmed by diluting in phosphate-buffered saline (PBS) and plating on SBA. Each well was inoculated with 5 μL of bacterial suspension. Negative control wells contained culture medium only, while positive control wells contained media inoculated with bacterial suspension. Further inoculated wells controlled for the antimicrobial effects of the greatest concentration of solvent (DMSO or ethanol) used in any of the test wells (ca. 10%). Microtitre plates were incubated anaerobically at 37° C. for 48 h, and then MICs were determined as the lowest concentration of each compound that prevented visible bacterial growth. MBCs were determined by plating 50 μL from each well showing no visible growth on to SBA and incubating these plates anaerobically at 37° C. for 96 h. The MBCs were the lowest concentration of each compound that killed >99.9% of the initial inoculum. MICs and MBCs were performed in duplicate.

Checkerboard Tests

Checkerboard assays were performed according to the standard protocol published by the American Society for Microbiology (American Society for Microbiology, 1992) to investigate the existence of synergistic anti-*P. acnes* interactions between EPA, GLA, and GLA 70% in combination with BPO, FUS, NEO and SA. Doubling dilutions of each compound were prepared in SBB and dispensed to 96-well plates in the standard checkerboard pattern. Concentrations of the compounds ranged from ≤1/16 XMIC to ≥4 XMIC. Positive control wells contained broth with the greatest volume of solvent used in any well, while negative control wells contained just broth. Inoculums were prepared to $1\times10^7$ CFU/mL as above. Each well (except for negative controls) was inoculated with 5 μL of bacterial suspension. Plates were incubated anaerobically at 37° C. for 48 h, and then each well was determined to contain growth or no growth based on the clarity of the broth and/or the presence of colonies in the well. The fractional inhibitory concentration (ΣFIC) for each well was determined for each interaction. The lowest ΣFIC values from duplicate plates of each drug-drug interaction were used to calculate a mean value from which the nature of each interaction was assessed. Synergy is defined as a ΣFIC≤0.5. To check for any bactericidal synergistic action, 10 μL from each well containing no visible growth was plated out on to SBA and incubated anaerobically at 37° C. for 48 h. In this report, bactericidal synergy is recognized when a combination of agents kills >99.9% of the inoculum at combined concentrations that are less than the cumulative MBCs of the compounds.

Results:
Activity of Test Agents Alone Against *P. acnes*

The MICs for EPA, GLA and GLA 70% against *P. acnes* ranged 64-128 mg/L, though none of these fatty acids killed the bacterium up to 4096 mg/L (Table 5). The MICs for SA and BPO were 64 mg/L, but neither of these agents was bactericidal up to 4096 mg/L. The MIC and MBC of FUS against *P. acnes* were 2 and 256 mg/L, respectively, and the MIC and MBC of NEO was 8 and 16 mg/L, respectively (Table 5). AZA showed no anti-*P. acnes* activity even at 4096 mg/L (Table 7). Ethanol and DMSO had no effect on the growth of *P. acnes* up to the maximum concentrations tested. It is important to note that GLA 70% was just as effective as GLA >95%.

TABLE 7

MIC and MBC for each of the test compounds against *P. acnes*.

| | Results (mg/L) | |
|---|---|---|
| Test Agent | MIC | MEC |
| EPA | 128 | >4096 |
| GLA | 64 | >4096 |
| GLA 70% | 64 | >4096 |
| SA | 64 | >4096 |
| AZA | >4096 | >4096 |
| BPO | 64 | >4096 |
| FUS | 2 | 256 |
| NEO | 8 | 16 |

Interactions between EPA, GLA and GLA 70% in combination with BPO, FUS, NEO and SA Checkerboard assays were used to detect synergy between the three fatty acids (EPA, GLA, and GLA 70%) and four conventional antimicrobial agents (BPO, NEO, FUS and SA). The lowest ΣFIC on each of duplicate checkerboards was used to calculate a mean ΣFIC for each interaction (Table 8). The only combination that showed a positive interaction/synergy in the control of *P. acnes* was EPA with SA.

TABLE 8

Mean fractional inhibitory concentration (ΣFIC) values for each interaction against *P. acnes*. n = 2; SD, standard deviation.

| Compounds tested | Results (ΣFIC) | |
|---|---|---|
| | Mean | SD |
| SA vs. EPA | 0.78 | 0.31 |
| SA vs. GLA | 1.38 | 0.88 |
| SA vs. GLA 70% | 2.00 | 0.00 |
| BPO vs. EPA | 2.00 | 0.00 |
| BPO vs. GLA | 2.00 | 0.00 |
| BPO vs. GLA 70% | 2.00 | 0.00 |
| FUS vs. EPA | 2.00 | 0.00 |
| FUS vs. GLA | 1.38 | 0.88 |
| FUS vs. GLA 70% | 2.00 | 0.00 |
| NEO vs. EPA | 1.50 | 0.71 |
| NEO vs. GLA | 1.50 | 0.71 |
| NEO vs. GLA 70% | 1.00 | 0.00 |

Example 10

Perceived Odor of Formulations A to C

A study was conducted to determine the perceived odor of the compositions of Formulations A to C as prepared according to Example 1. A small amount of each of the compositions was randomly applied to the back of the hand or wrist of each of four participating subjects. Each subject reported the level of "fishy" odor over several minutes on a Lichert-type scale as shown in Table 9 below.

TABLE 9

Odor Levels of Formulations A to C.

| Formulation | Low | Low (Avg.) | Medium | Medium (Avg.) | High | High (Avg.) |
|---|---|---|---|---|---|---|
| A | +, −, −, + | −/+ | ++, +, +, ++ | +/++ | +++, ++, ++, +++ | ++/+++ |
| B | +, −, −, + | −/+ | ++, +, +, ++ | +/++ | +++, ++, ++, +++ | ++/+++ |
| C, | −, −, −, − | − | −, −, −, − | − | +, −, +, + | + |

These study data indicate that the composition of Formulation C surprisingly has a cosmetically acceptable odor (e.g., is free of unpleasant odors), whereas the compositions of Formulation A or Formulation B at the same levels of EPA and GLA free fatty acids.

While the present disclosure has been described and illustrated herein by references to various specific materials, procedures and examples, it is understood that the disclosure is not restricted to the particular combinations of materials and procedures selected for that purpose. Numerous variations of such details can be implied as will be appreciated by those skilled in the art. It is intended that the specification and examples be considered as exemplary, only, with the true scope and spirit of the disclosure being indicated by the following claims. All references, patents, and patent applications referred to in this application are herein incorporated by reference in their entirety.

What is claimed is:

1. A topical composition comprising eicosapentaenoic acid and salicylic acid, wherein the purity of the eicosapentaenoic acid is at least 95% by weight eicosapentaenoic acid in its free acid form.

2. The composition of claim 1 further comprising gamma-linolenic acid in the free acid form.

3. The composition of claim 1, further comprising ascorbyl palmitate.

4. The composition of claim 3, further comprising NaOH.

5. The composition of claim 1, comprising ≤5 weight % eicosapentaenoic free acid, by weight of the composition.

6. The composition of claim 5, comprising about 0.5 weight % to about 4.08 weight % eicosapentaenoic free acid.

7. The composition of claim 2, wherein the purity of the gamma-linolenic acid is at least 70% by weight gamma-linolenic free acid.

8. The composition of claim 2, wherein the weight ratio of eicosapentaenoic free acid to gamma-linolenic free acid is about 8:1 to about 2:1.

9. The composition of claim 8, wherein the weight ratio of eicosapentaenoic free acid to gamma-linolenic free acid is about 4:1.

10. The composition of claim 2, comprising about 0.1 weight % to about 3 weight % gamma-linolenic free acid, by weight of the composition.

11. The composition of claim 1 comprising about 0.1 weight % to about 5 weight % salicylic acid, by weight of the composition.

12. The composition of claim 1 that is free of unpleasant odor.

13. A topical composition devoid of unpleasant odor comprising:
eicosapentaenoic free acid;
gamma-linolenic free acid; and
salicylic acid,
wherein the composition has a weight ratio of eicosapentaenoic free acid to gamma linolenic free acid of about 8:1 to about 4:1; and
the eicosapentaenoic free acid and the gamma linolenic free acid are present in a combined amount not greater than 5 weight % of the composition.

14. The composition of claim 13 further comprising ascorbyl palmitate.

15. The composition of claim 13, wherein the purity of the eicosapentaenoic acid is at least 95 weight % eicosapentaenoic free acid and the purity of the gamma-linolenic acid is at least 70 weight % gamma-linolenic free acid.

16. The composition of claim 13, comprising no more than 5 weight % salicylic acid, by weight of the composition.

17. A method of ameliorating a skin disease or disorder in a subject, wherein the skin disease or disorder is selected from the group consisting of dryness, roughness, wrinkles, sunburn, seborrheic dermatitis and acne, the method comprising topically administering a composition of claim 1 to at least a portion of the skin of the subject.

18. The method of claim 17, wherein the skin disease or disorder is acne.

19. The method of claim 17, wherein the skin disease or disorder is wrinkles.

20. The method of claim 17, wherein the skin disease or disorder is seborrheic dermatitis.

* * * * *